US009993365B2

United States Patent
Platt et al.

(10) Patent No.: US 9,993,365 B2
(45) Date of Patent: Jun. 12, 2018

(54) SURGICAL HEATING AND COOLING SYSTEM AND DEVICES AND METHODS FOR THE USE THEREOF

(71) Applicants: Douglas E. Platt, Bryan, TX (US); Robin A. Pate, Bryan, TX (US); Jon L. Gardner, Bryan, TX (US)

(72) Inventors: Douglas E. Platt, Bryan, TX (US); Robin A. Pate, Bryan, TX (US); Jon L. Gardner, Bryan, TX (US)

( * ) Notice: Subject to any disclaimer, the term of this patent is extended or adjusted under 35 U.S.C. 154(b) by 0 days. days.

(21) Appl. No.: 15/063,598

(22) Filed: Mar. 8, 2016

(65) Prior Publication Data
US 2016/0184132 A1    Jun. 30, 2016

Related U.S. Application Data

(63) Continuation of application No. 13/429,303, filed on Mar. 23, 2012, now Pat. No. 9,314,366.

(60) Provisional application No. 61/466,910, filed on Mar. 23, 2011.

(51) Int. Cl.
*A61M 37/00*     (2006.01)
*A61F 7/00*      (2006.01)
*A61M 1/36*      (2006.01)

(52) U.S. Cl.
CPC .......... *A61F 7/0085* (2013.01); *A61M 1/369* (2013.01); *A61M 1/3666* (2013.01); *A61M 1/3667* (2014.02); *A61M 1/3664* (2013.01); *A61M 2205/3606* (2013.01); *A61M 2205/366* (2013.01); *A61M 2209/084* (2013.01)

(58) Field of Classification Search
CPC . A61F 7/0085; A61M 1/3667; A61M 1/3666; A61M 1/369; A61M 1/3664; A61M 2205/3606; A61M 2205/366; A61M 2205/084
See application file for complete search history.

(56) References Cited

U.S. PATENT DOCUMENTS

| 3,423,275 | A    | 1/1969  | Honda et al.   |       |
|-----------|------|---------|----------------|-------|
| 6,413,233 | B1   | 7/2002  | Sites et al.   |       |
| 6,613,008 | B2   | 9/2003  | Aboul-Hosn et al. | |
| 7,403,704 | B2   | 7/2008  | Eccleston et al. | |
| 7,588,549 | B2   | 9/2009  | Eccleston      |       |
| 8,529,489 | B2 * | 9/2013  | Ruzicka et al. ..... A61M 1/3672 604/6.13 |
| 2002/0085952 | A1 * | 7/2002 | Ellingboe ........... A61M 1/3621 422/45 |

(Continued)

OTHER PUBLICATIONS

Nolan, J.P., et al., "Therapeutic Hypothermia After Cardiac Arrest: An Advisory Statement by the Advanced Life Support Task Force of the International Liaison Committee on Resuscitation," Circulation, Jul. 8, 2003, pp. 118-121, copyright 2003 by the American Heart Association, Inc, and Elsevier Science Ireland Ltd.

(Continued)

*Primary Examiner* — Philip R Wiest
(74) *Attorney, Agent, or Firm* — Jones Walker, LLP (57) ABSTRACT

A modular cooling-heating system for use in the controlled delivery of temperature-controlled fluids to a heat exchanger associated with the blood of a patient undergoing a medical procedure is described, wherein the cooling-heating system uses adaptive temperature control protocols.

12 Claims, 6 Drawing Sheets

(56) References Cited

U.S. PATENT DOCUMENTS

2006/0025755 A1    2/2006  Landman et al.

OTHER PUBLICATIONS

Polderman, K.H., "Application of therapeutic hypothermia in the intensive care unit," Intensive Care Medicine, copyright 2004 by Springer-Verlag.
Bernard, S., et al., abstract from "Induced hypothermia using large volume, ice-cold intravenous fluid in comatose survivors of out-of-hospital cardiac arrest: a preliminary report," Resuscitation, Jan. 2003, [retrieved from the Internet on Mar. 26, 2014 using <URL: http://www.ncbi.nlm.nih.gov/pubmed/?term=Resuscitation%2C+Vol.+56%2C+pp.+9-13+(2003).>].
De Georgia, M.A., "Cooling for Acute Ischemic Brain Damage (COOL AID)—A feasibility trial of endovascular cooling," Neurology, Jul. 2004, pp. 312-317, copyright 2004 by AAN Enterprises, Inc.
Hachimi-Idrissi, S., et al., abstract from "Mild hypothermia induced by a helmet device: a clinical feasibility study," Resuscitation, Dec. 2001, [retrieved from the Internet on Mar. 26, 2014 using <URL: http://www.resuscitationjournal.com/article/S0300-9572(01)00412-9/abstract>].
Simosa, H.F., et al., abstract from "Increased risk of deep venous thrombosis with endovascular cooling in patients with traumatic head injury," [retrieved from the Internet on Mar. 26, 2014 using <URL: http://www.ncbi.nlm.nih.gov/pubmed/?term=simosa+the+american+surgeon>].

\* cited by examiner

SURGICAL HEATING AND COOLING SYSTEM AND DEVICES AND METHODS FOR THE USE THEREOF

CROSS REFERENCE TO RELATED APPLICATIONS

This application claims priority to U.S. Provisional patent application Ser. No. 61/466,910, filed Mar. 23, 2011, the contents of which are incorporated by reference herein in their entirety.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The inventions disclosed and taught herein relate generally to heating and cooling systems and method of use during surgery and, more specifically, relates to a system and method of use for the controlled heating and/or cooling of an internal organ or tissue of a patient before and during surgery.

Description of the Related Art

Under normal circumstances, the human body maintains a near-constant temperature of about 37 degrees Celsius (° C.) or about 98.6 degrees Fahrenheit (° F.), thereby maintaining a delicate balance that optimizes cellular functions and biochemical reactions, while simultaneously balancing the heat lost to the environment by heat produced within the body.

There are a number of instances, however, where medical intervention is required to manipulate the core human body temperature of a patient. Particularly, there are circumstances under which a patient will need to be cooled in a rapid manner to thwart the onset of serious, and often fatal, repercussions. For instance, a patient may be suffering from malignant hyperthermia, a life threatening elevation in body temperature experienced by some patients after receipt of certain muscle relaxants and general anesthetics during surgery. This situation is called a pharnacogenetic reaction; a variation in drug response caused by hereditary factors. Such a rapidly progressive reaction is often fatal, and requires immediately initiated treatment. This condition can be reversed if the patient's core body temperature is immediately lowered to within acceptable parameters.

By slowing down a patient's metabolism, the demand for oxygen and nutrients can be minimized until appropriate treatment is effectuated. A dangerously high core body temperature is often due to infection, tumor necrosis, or malignant hyperthermia.

Such conditions result in harmful fluid and electrolyte imbalances, increased cellular metabolic rates, and cognitive impairment. If not immediately addressed, a patient may suffer irreversible cellular injury, loss of brain and liver cells, and ultimately may suffer critical organ failure resulting in death.

Evidence suggests that patient cooling provides beneficial protection against further deterioration of patient health in instances of cardiac arrest, surgery on the brain blood vessels, stroke, traumatic injury, or open heart operations. Cooling the blood before or during such events has been found to substantially decrease the severity of the resulting injury to the patient.

The introduction of moderate hypothermia (28° C. to 32° C.) before cardiac arrest has been successfully used since the 1950's to protect the brain against the global ischemia that occurs during some open-heart surgeries. Recently, the American Heart Association and others have recommended that some victims of heart attacks be chilled using induced hypothermia [Polderman, K., *Intensive Care Medicine*, Vol. 30(4), pp. 556-575 (2004)]. There are about 250,000 to 300,000 people suffering from cardiac arrest in the United States yearly, with about 50,000 to 75,000 making it to the hospital with adequate time for blood cooling to protect the brain and heart from further injury. The International Liaison Committee on Resuscitation (ILCOR) ALS (Advanced Life Support) Task Force has recommended, in view of this and other information, that such cooling is beneficial for cardiac arrest patients, as well as patients suffering from other cardiac rhythm disorders [Nolan, J. P., et al., *Circulation*, Vol. 108, pp. 118-121 (2003)].

Although the benefits of patient cooling are well known, existing methods and systems are cumbersome, ineffective, and often inadequate for rapid patient cooling. Often, these cooling methods use an average "weight load" for a patient, which can result in over-shooting the desired temperature range, which in turn can lead to problems in correcting the temperature, and in some instances, harm to the patient as a result of the temperature over-shoot.

Current methods of cooling treatment include crude improvised solutions such as packing a patient in ice; immersing the patient in cool water; applying ice packs to the groin, axillae, neck, and other regions of the patient; or the use of a cooling helmet [Hachimi-Idrissi, S., et al., *Resuscitation*, Vol. 51, pp. 275-281 (2001)]. Naturally, it is seen that such techniques, although well-intentioned, do not provide for rapid body temperature cooling as often required in surgery and Intensive care situations. Such treatment is difficult and labor intensive and cannot be performed in medical cases where time is of the essence.

Other attempts at patient cooling have included convective thermal blankets, room coolers, and other similar external cooling mechanisms. Although such devices do assist in cooling the environment surrounding a patient, they are generally ineffective in adequately reducing a patient's core body temperature, and do not allow for any control of the cooling of a patient. Furthermore, such methods generally produce unwanted patient shivering and discomfort which may even lead to an increase in core body temperature.

Evaporative cooling has also been attempted by wetting a patient's skin or clothing and allowing the water, or other liquid, to evaporate and remove heat from the body. Such treatment generally includes sponge baths and is sometimes combined with enhanced room air circulation to increase the rate of evaporation. Such cooling is not practical in intensive care situations, is extremely time-consuming and labor intensive, and inadequate for serious life-threatening conditions.

A variety of surgical patient blood cooling methods and systems are also available. Such treatment generally involves the use of cooling catheters inserted into a vein for direct cooling of a patient's blood through the use of cooled saline, wherein the saline cools the patient's whole body by lowering the temperature of a patient's blood at a rate of about 1° C.-2° C/ hour. The intravenous infusion of crystalloid at 4° C. over time to reduce core temperature has also been described [Bernard, S., et al., *Resuscitation*, Vol. 56, pp. 9-13 (2003)]. Such devices and approaches, while efficient, are invasive and require surgical incision. The invasive surgical treatment required by such devices require substantial time and skill to administer properly, force patients to undergo additional pain and discomfort, introduce the risk of contamination and blood clotting, and have been cost-prohibitive and impractical in use. Other adverse events associated with this type of technique include bleeding, infection, vasculature puncture, and the potential for deep vein thrombosis (DVT) [See, for example, Simosa, H. F., et al., *The American Surgeon*, Vol. 73 (5), pp. 461-464 (2007)].

In these respects, the patient cooling system for medical treatment of the present invention substantially departs from the conventional concepts and designs of the prior art, and in so doing, provides a system and method capable of both reducing and elevating patient body and organ temperature in a controlled yet substantially safe, cost-effective, and practical manner.

The inventions disclosed and taught herein are directed to an improved system for both heating and/or cooling a patient during a surgical procedure, as well as an improved thermoelectric device capable of both cooling and heating.

BRIEF SUMMARY OF THE INVENTION

The objects described above and other advantages and features of the invention are incorporated in a method and a system that provides for a modular cooling-heating system for use in supplying temperature-controlled fluids to heat exchangers during surgical operations, in order to assist in controlling the patient's temperature during the operation. The modular nature of the system allows it to be coupled with other components, such as refrigerator or ice-cooling units in the operating room in a single, compact footprint. The temperature control by the system uses an adaptive temperature control protocol that looks at a series of variables and adjusts the rate of fluid flow so as to effect controlled cooling or controlled heating of the patient without over-shooting the target temperature setpoints.

In accordance with a first aspect of the present disclosure, a modular cooling-heating system for the controlled delivery of fluids to heat-exchange devices in a surgical setting so as to assist in controlling the body temperature of a patient during a medical procedure is described, the system comprising a first unit including a pump for pumping fluid to a heater exchanger and at least one fluid reservoir; a second unit associated with the first unit and including a computer system including an adaptive temperature control software protocol for controlling the temperature range of the fluid pumped to the heat exchanger; and two or more heaters for heating the fluid; wherein the cooling-heating system is in fluid communication with the heat-exchange device.

In accordance with a further aspect of the present disclosure, a modular support device for a cooling-heating assembly, a blood reservoir, an oxygenator, a blood filter and a plurality of tubing sections that are in fluid communication with each other is described, wherein the modular support device comprises a chassis having a planar surface; support means for removably mounting and supporting the cooling-heating assembly, the blood reservoir, oxygenator and/or the blood filter in close proximity on the chassis; and, a plurality of casters attached to the chassis for moving the support device.

BRIEF DESCRIPTION OF THE SEVERAL VIEWS OF THE DRAWINGS

The following figures form part of the present specification and are included to further demonstrate certain aspects of the present invention. The invention may be better understood by reference to one or more of these figures in combination with the detailed description of specific embodiments presented herein.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

Definitions

The following definitions are provided in order to aid those skilled in the art in understanding the detailed description of the present invention.

The term "cardioplegia" as used herein refers to a common technique in cardiopulmonary bypass operations, wherein a cold solution is injected into a patient's coronary arteries, so as to slow down and "arrest" the heart. Cardioplegia may be warm or cold blooded, and act to reduce oxygen consumption in the working heart of a patient. Typically, hypothermic blood cardioplegia given every 15 to 30 minutes provides a bloodless operative field and reduces oxygen consumption an additional 5% to 20%. Continuous warm cardioplegia avoids the deleterious effects of hypothermic ischemia and minimizes reperfusion injury. Perfusion may be interrupted for 5 to 10 minutes to allow adequate visualization of the operative site. Both warm and cold cardioplegia can be given either antegrade or retrograde, in accordance with the present disclosure.

The term "therapeutic hypothermia," as used herein, refers to a medical treatment protocol of lowering a patient's body temperature in order to aid in the reduction of the risk of ischemic injury to tissue following a period of insufficient blood flow, or during a surgical operation. Such induced hypothermia may be used to prevent or attenuate neurological injury, to provide neuroprotection in traumatic brain injury, cardiopulmonary resuscitation, stroke, and various other disorders, as well as to prevent or attenuate injury during surgical operations.

As used herein, the term "patient" refers to warm-blooded animals or mammals, and in particular humans, who are in need of medical therapy.

DETAILED DESCRIPTION

The Figures described above and the written description of specific structures and functions below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

Particular embodiments of the invention may be described below with reference to block diagrams and/or operational illustrations of methods. It will be understood that each block of the block diagrams and/or operational illustrations, and combinations of blocks in the block diagrams and/or operational illustrations, can be implemented by analog and/or digital hardware, and/or computer program instructions. Such computer program instructions may be provided to a processor of a general-purpose computer, special purpose computer, ASIC, and/or other programmable data processing system. The executed instructions may create structures and functions for implementing the actions specified in the block diagrams and/or operational illustrations. In some alternate implementations, the functions/actions/structures noted in the figures may occur out of the order noted in the block diagrams and/or operational illustrations. For example, two operations shown as occurring in succession, in fact, may be executed substantially concurrently or the operations may be executed in the reverse order, depending upon the functionality/acts/structure involved.

Computer programs for use with or by the embodiments disclosed herein may be written in an object oriented programming language, conventional procedural programming language, or lower-level code, such as assembly language and/or microcode. The program may be executed entirely on a single processor and/or across multiple processors, as a stand-alone software package or as part of another software package.

Applicants have created a system for cooling a body part/region, organ, or area of tissue of a patient or subject during a surgical operation wherein the system has an adaptive temperature control delivery assembly for imparting a controlled rate of cooling to a patient or region thereof. The system also includes a cooling solution transport system for transporting a cooling solution from the system to the patient, and an applicator that is configured for receiving the cooling or heating solution from the supply line. The transport system can include a supply line or conduit and a recycle line through which the cooling solution is transported.

Figure 1:
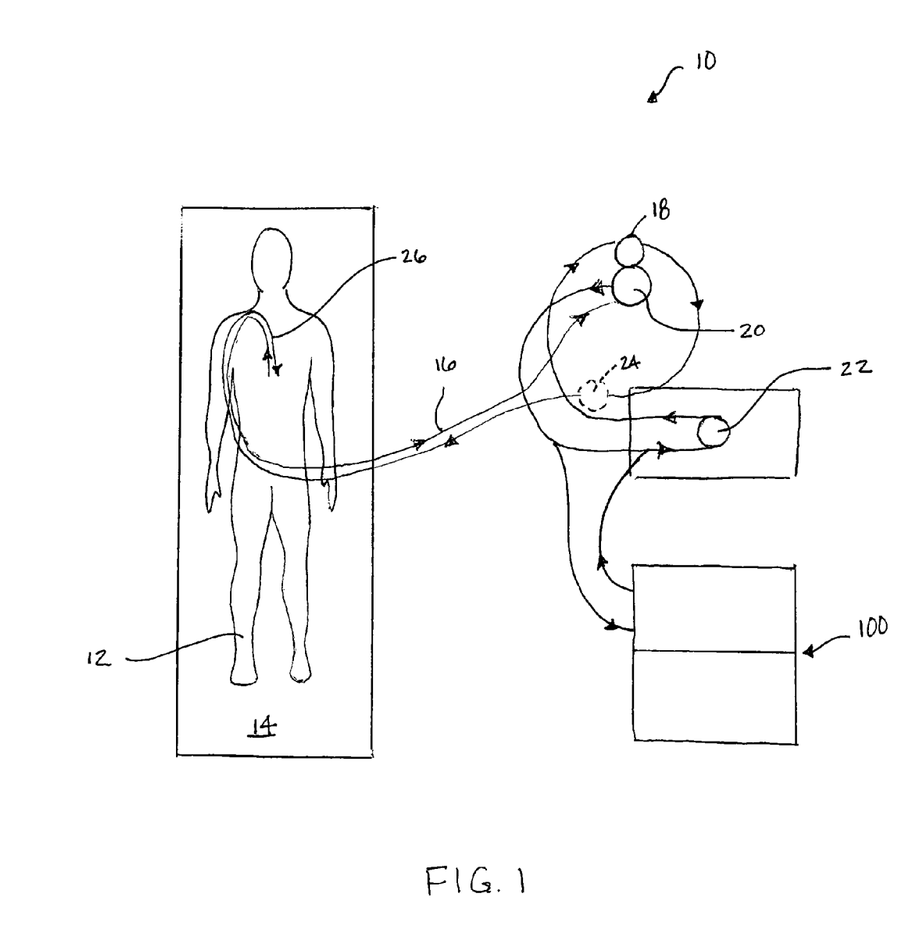
FIG. 1 illustrates a simplified diagram of a temperature control system in accordance with aspects of the present disclosure.

Turning now to the figures, FIG. 1 is an illustration of a general embodiment of the present disclosure in association with a typical cardiopulmonary bypass (CPB) operation, wherein a mechanical bypass of the heart and lungs is employed, such as in the case of cardiovascular and cardiac surgery. A cardiopulmonary bypass circuit is composed of two primary technologies: mechanical circulation of blood during temporary heart arrest, and artificial oxygenation of blood while blood flow is excluded from the lungs. FIG. 1 illustrates a typical CPB circuit 10 within a typical operating room setting. Blood is removed from a patient 12 on operating table 14 through use of a venous cannula 16 or similar device inserted into the inferior and superior vena cava using gravity or vacuum assisted venous drainage into a venous reservoir 20. The venous reservoir 20 may receive venous return in addition to field suction return (blood recovery via roller pump or vacuum activated suction wands). Alternatively, cell-washing technology (not shown) may be employed prior to the return of blood to the patient. An arterial pump 22, typically a remote mounted roller or centrifugal style pump, pulls blood from the venous reservoir 20 and pushes the blood into an oxygenator 18. Oxygenator 18 may further include or be connected to a heat exchanger (not shown) or other suitable temperature controller for use in raising or lowering the temperature of the patient's blood before it is reintroduced back into the patient. The arterial pump 20 is most often located on a separate rack, such as a heart-lung machine, behind the main or assisting physician in the operating room. Oxyhemoglobin can be created in the oxygenator 18, most commonly through use of a porous hollow fiber capillary material with blood flowing around the fibers and oxygen flowing through the fibers. Pressure from the arterial pump 22 continues to move blood out the oxygenator 18 through an optional arterial filter 24. The arterial filter 24 serves as a final filter for possible air and particulate introduced through the circuit. Blood is returned to the patient via the arterial cannula 26, usually placed in the patient's aorta. A modular cooler-heater (MCH) apparatus 100 in accordance with the present disclosure is in fluid communication with the Cardiopulmonary by-pass heat exchangers and other cooling systems associated with the CPB circuit 10, and provides temperature controlled fluids to a heat exchanger, typically integrated with oxygenator 18.

Figure 2:
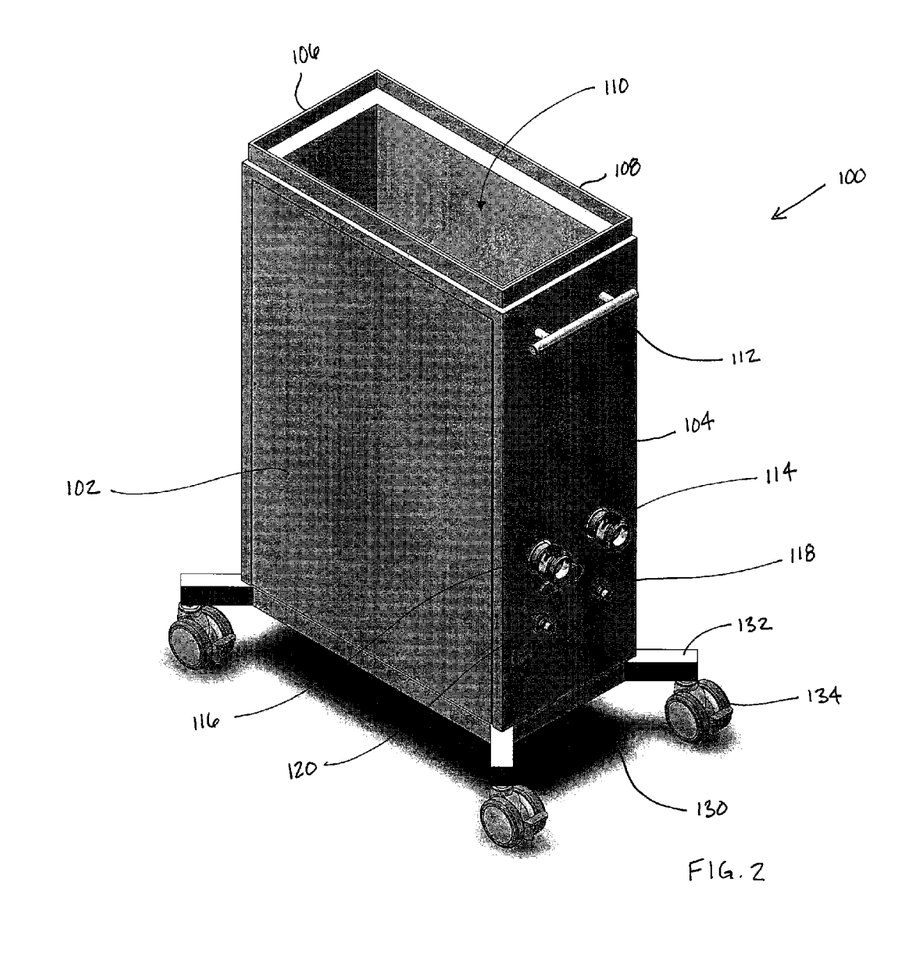
FIG. 2 illustrates an exemplary modular heating and cooling system for use in accordance with aspects of the present disclosure.
Figure 3:
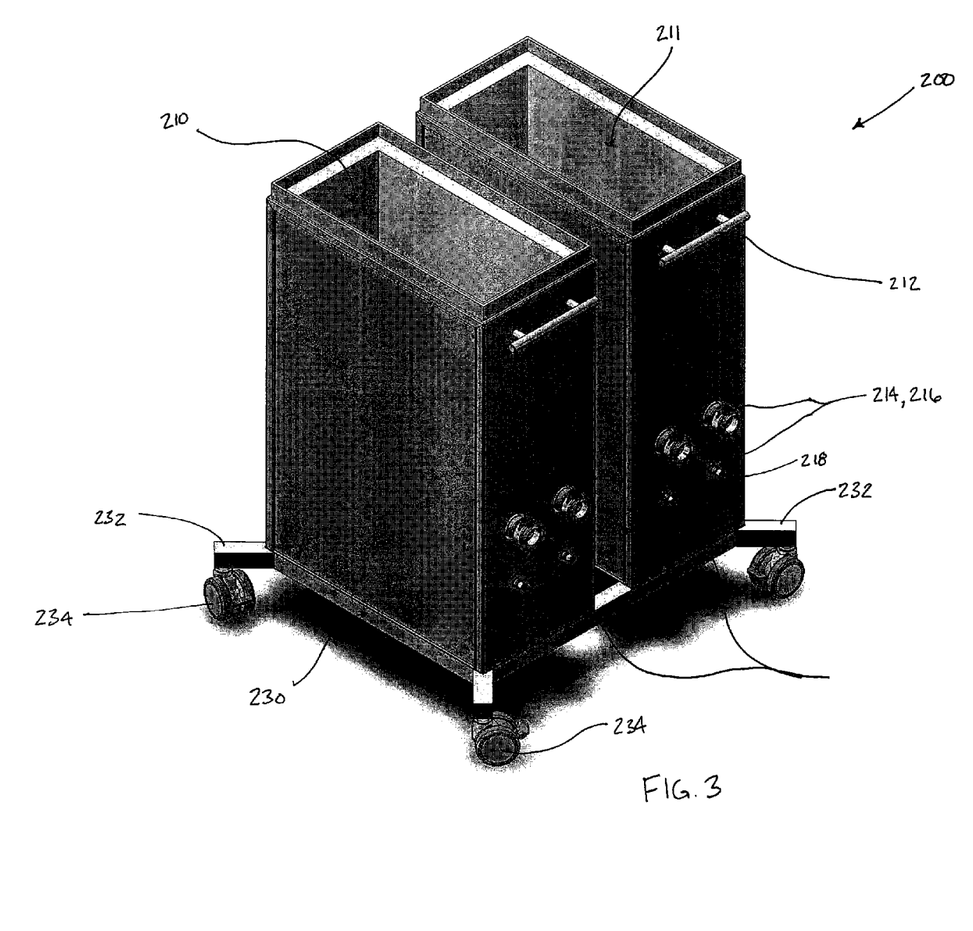
FIG. 3 illustrates an alternative embodiment of the present disclosure which includes a dual unit assembly.

System Overview:

FIG. 2 illustrates an isometric view of an exemplary modular cooler-heater 100 in accordance with the present disclosure. FIG. 3 illustrates an alternative embodiment associated with the cooler-heater of the present disclosure. These figures will be discussed in combination with each other.

The modular cooler-heater (MCH) 100 is a set of devices used to pump temperature controlled fluid, such as water, ice-water, or other appropriate fluids, to a heat exchanger during cardiovascular surgery or other medical procedures where therapeutic hypothermia would be beneficial, in a medical operating room environment. The overall system in accordance with the present disclosure consists of a least one local unit 100, a remote unit 300 (see FIG. 4), and a modular support device that comprises the unit chassis 130, caster supports 132, and casters 134. The chassis 130 may be rigid or flexible, and made from a variety of materials, including polymeric materials, surgical-grade stainless steel, and the like, and is preferably made of a material that is sterilizable.

The unit 100 includes a fluid retention chamber 110 defined by oppositely-spaced side walls 102 and 108, a planar bottom (not shown), and front and back walls 104 and 106, respectively, wherein the walls are arranged perpendicular to each other. On the bottom of the unit 100 is a modular chassis unit 130, which comprises front and rear caster supports 132, and casters or wheels 134. The chassis may also include a plurality of retainers so allow the fluid retention chamber to be attached to the chassis, such suitable retainers including straps, clips, hooks, and the like, as appropriate. A handle 112 is attached to at least one face of the unit 100, allowing for directing the travel of the unit as it is rolled on its casters, and/or for mounting the remote unit 300, as appropriate. The front wall 104 also includes fluid inlet and outlet couplings 114 and 116, respectively, for attaching fluid transfer lines (not shown) to the unit, as well as pressure lines 118, 120. At least one wall of the unit 100, such as front wall 104, further includes a data receiving port allowing a hardwire information and data communication tether to be attached, allowing for the use of a cooler-heater remote unit (300) by the operator to control the temperature of the fluids, as will be discussed in association with FIG. 4.

The units can be interchanged to provide the optimum device configuration for the operator, such as a cardiovascular perfusionist. There are normally two cooler-heaters used in open-heart surgery, one for the main or arterial heat exchanger and one for the auxiliary or cardioplegia heat exchanger. The modular cooling-heating system 100 of the present disclosure allows the operator to configure the cooler-heaters for specific case needs (cooling type) and/or operating room constraints.

The modular cooling-heating local unit 100 provides the pump, valving, heater, power supply and fluid connections and is the main unit of the system. There are two different type of local units, a refrigeration unit and an ice unit. The refrigeration unit uses an electro-mechanical refrigeration unit to provide cooling for the device, while the ice unit utilizes an ice bath, in which ice may be externally supplied, or made using an integrated ice-making system, so as to provide cooling features. These different types are selected by the operator based on specific cooling requirements for either the main heat exchanger (e.g., an arterial line) or the auxiliary heat exchanger (e.g., a cardioplegia line). Common usage is for a refrigeration unit to be used on the arterial line and an ice unit to be used on the cardioplegia line, as the ice unit normally can hold colder temperatures longer. The fluid pumped by the MCH is controlled in tenth degree increments (0.1° C.) over a range from about 0° C. to about 48° C., +/−0.3° C., preferably in a range from about 0° C. to about 43° C., +/−0.3° C. An over-temperature alarm is included within the system to deactivate the system at 42.5° C. A redundant over-limit controller in the local unit provides an additional runaway temperature alarm at 43° C. Fluid is pumped in a closed- or open-loop type manner, from pressures ranging from ambient to about 12 psi (621 torr). Heating in the local unit is provided by two electric heaters, one at 500 watts the second at 1000 watts. These heaters are placed in the fluid recirculation path and are activated separately to warm the water. Cooling in the local unit is facilitated by a single valve routing the water from the recirculation path to the ice bath or the refrigeration bath.

Figure 5A:
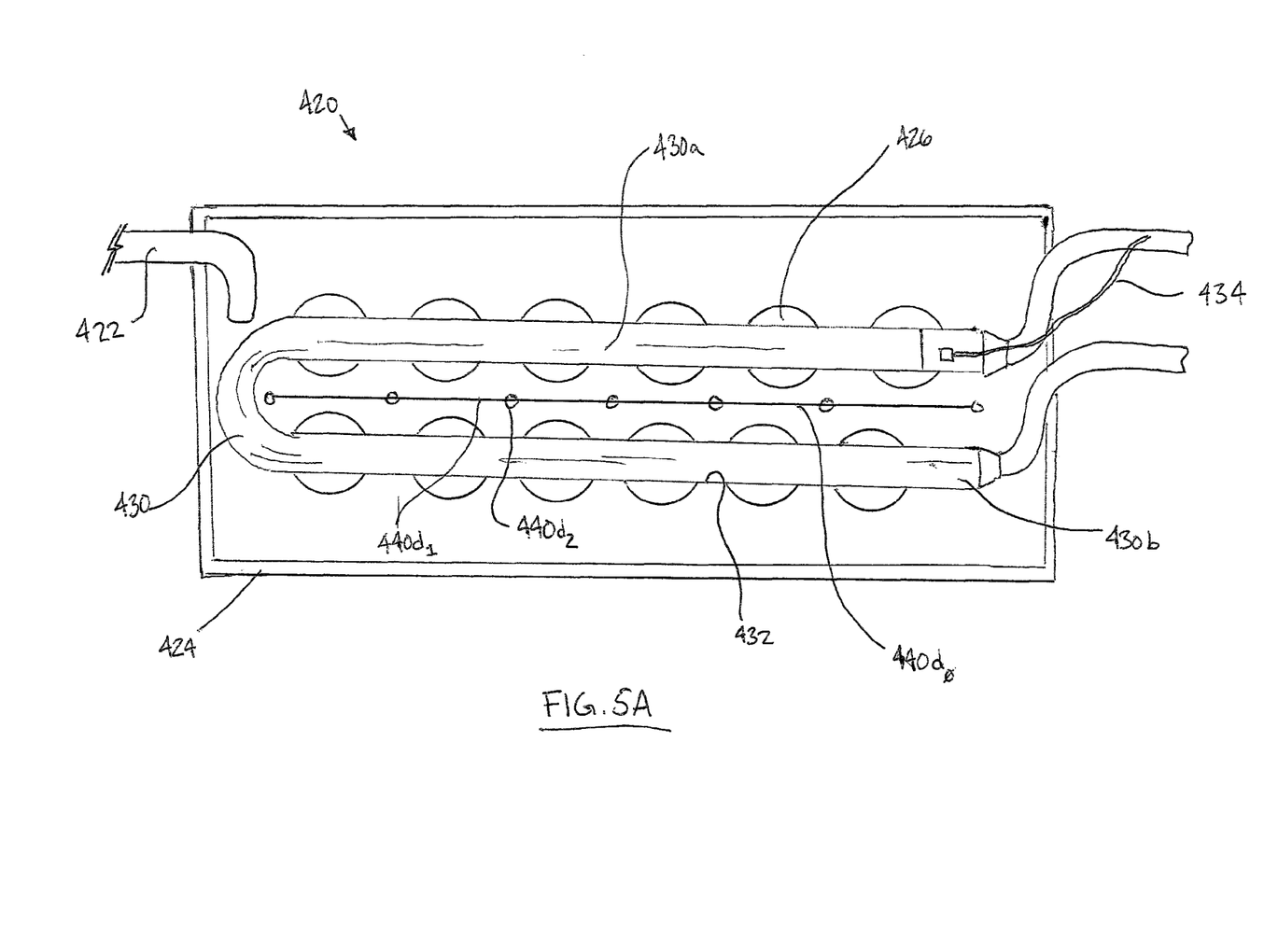
FIG. 5A illustrates an exemplary ice maker in association with embodiments of the present disclosure.
Figure 5B:
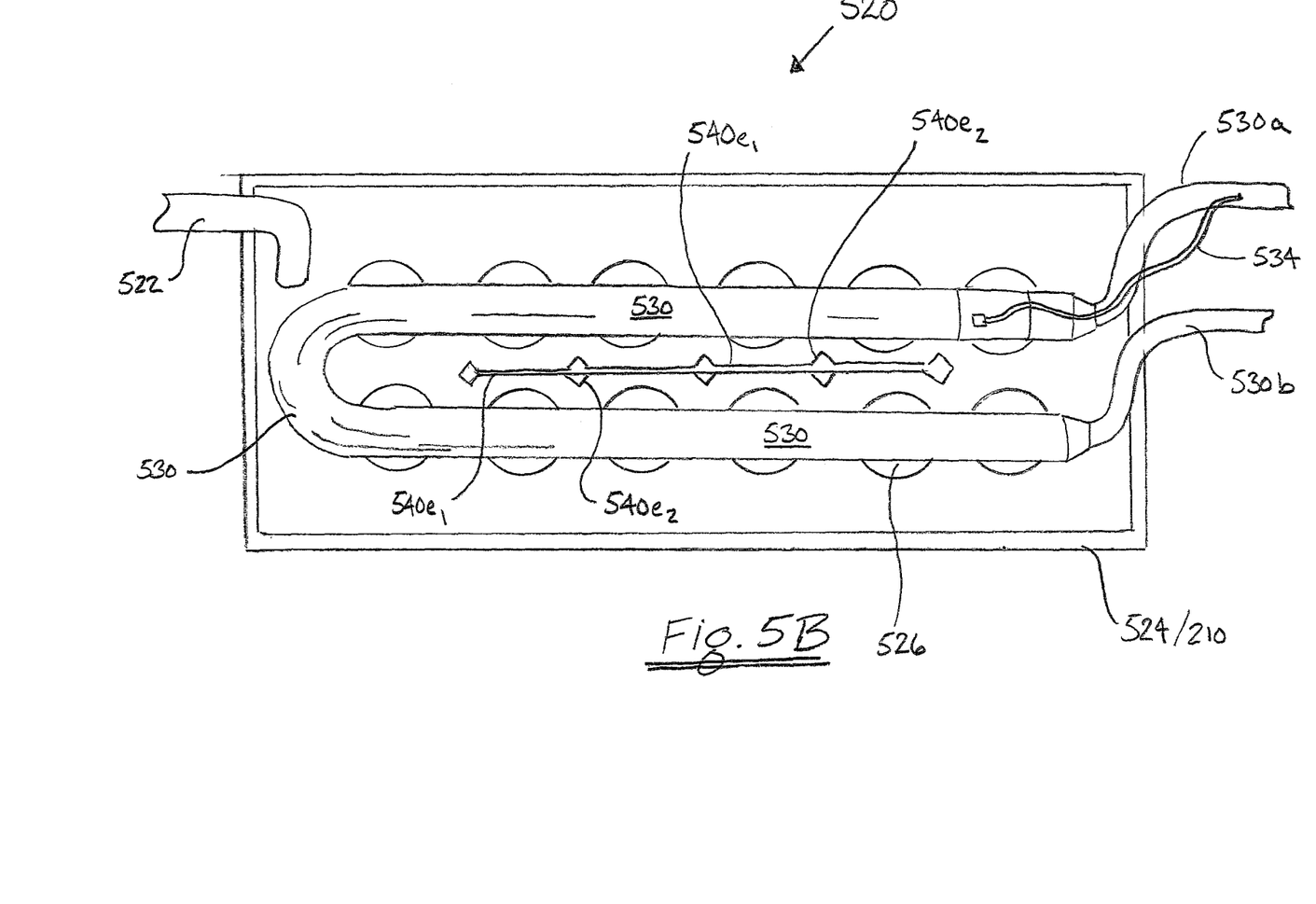
FIG. 5B illustrates another exemplary ice maker in association with embodiments of the present disclosure.

As referenced above, the ice bath portion of the unit 100 may include an ice maker, which may operate in a number of manners, includes filling a selected container within the unit with water, or filling a container within the unit with multiple compartments, removing the heat from the water in all the compartments, and ejecting one or more ice cubes. Another way to make ice cubes within the unit itself, in accordance with the present disclosure, involves using a multiple finger evaporator where the closed ends are suspended in a water bath. As the ice making operation progresses, the refrigerant within the evaporator tube fingers chills the water surrounding each of the fingers, causing it to freeze and form an increasingly thick wall. Typically, the evaporator chills the water for a period of time sufficient to fully freeze the ice cube. Completely frozen ice cubes are ejected, and after ejection another cycle of the ice maker begins. A general illustration of the embodiment of the use of an integrated ice-making assembly within the system is shown in FIG. 5, which illustrates the use of an ice making assembly with a capacitive sensor in association with one or more evaporator tubes.

As will be discussed below, ice making assemblies having evaporator tubes proximate to the ice can use a tube as one electrode of a two-electrode capacitor. However, the present invention is not limited to using a refrigerant evaporator tube as one capacitive electrode. The present invention also contemplates those embodiments in which other portions of the ice making apparatus are used as one electrode in a capacitive sensor. Preferably, the part of the ice maker selected as a capacitive electrode should have good conductivity and be located proximate to at least one location where ice is formed within the unit.

In some aspects of the present invention, a second electrode of the capacitive ice sensor is a conductor which is placed in the ice making container, such as fluid retention chamber 210, in a pattern corresponding to the location and shape of the formed ice. As one example, the second electrode can be a wire, foil, tube, or other cross-sectional shape which is suspended within the ice making container, embedded in the walls or other structure of the container, adhered to the container, coated on a surface of the container, or otherwise placed in locations which correspond to formation of ice by some form of contact with the container. However, it should be pointed out that the embodiments of the present invention are not constrained to the use of a second electrode as described. The present invention also contemplate those embodiments in which the second electrode is a second part of the ice making assembly, such as a fluid retention chamber, or fluid container, wall or other structure, water inlet, or other component. Preferably, the second electrode is not in electrical communication with the first electrode, except for the capacitive field of the water being frozen.

In some embodiments of the present invention, ice can be formed proximate to an evaporator of a refrigeration unit, the evaporator being suspended within a bath, of liquid water, such as within fluid retention chamber 210 or the equivalent. The wall thickness of the ice continues to increase as cold refrigerant is pumped through the evaporator. In those embodiments where the evaporator has a plurality of downward-depending fingers, the ice forms around the individual fingers, and the wall thickness of these individual ice shapes continues to increase as more time is spent with a sub-freezing evaporator.

By monitoring the wall thickness of the forming ice with a capacitive sensor, the ice making process can be terminated at a time when the measured ice wall thickness (as inferred from the change in capacitance) is within a predetermined range, thereby allowing for added temperature control by the operator. At that time, the sub-freezing temperature of the evaporator tube is ended as a result of the electronic controller's operation of the refrigerant unit, and the evaporator tube can be warmed to permit the ice shape to be released from the finger.

Turning now to the figures associated with the ice-making features of the assemblies of the present disclosure, FIG. 5A generally illustrates an ice making system 420 according to one, non-limiting embodiment of the present invention. Ice making system 420 includes a capacitive ice sensor in which the first electrode is evaporator tube 430 along with its associated, depending fingers 432. A lead wire 434 is in electrical communication with evaporator tube 430, and may be separately or simultaneously (shown) in electrical communication with appropriate capacitive measurement circuitry. The second electrode of the capacitive ice sensor comprises a conductor assembly $440d_0$ placed centrally within the U-shape of evaporator tube 430 and within container 424, which may be a fluid retention chamber such as chambers 110 or 210 as discussed in association with FIGS. 2 and 3. It should be noted that while the evaporator tube is shown to be U-shaped, those of skill in the art will realize that it may be of any appropriate shape. Conductor assembly $440d_0$ include a plurality of downwardly depending (into the paper, as viewed from FIG. 5A) pins $440d_2$ which extend along at least part of the height of the evaporator fingers 432. Pins $440d_2$ are interconnected by a wire $440d_1$ or other appropriate inter-connector. Conductor assembly $440d_0$ is in electrical communication with the capacitive measurement circuitry. In one embodiment, a pin $440d_2$ may be present along either side of the finger, such that a two by six array of fingers 432 would have seven pins as shown in FIG. 5A. However, the present invention contemplates as few as one pin which is placed proximate a region in which an ice cube is to be formed.

FIG. 5B depicts another alternative ice making system 520 according to one aspect of the present invention. Ice making system 520 includes a capacitive ice sensor in association with fluid retention chamber (e.g., 210) in which the first electrode assembly is evaporator tube 530 along with its fingers 532. A lead wire 534 is in electrical communication with evaporator tube 530, and is also in electrical communication with the capacitive measurement circuitry. The second electrode of the capacitive ice sensor comprises a conductive assembly $540e_0$ placed centrally within the center of the U-shape of evaporator tube 530 and within container 524. In one embodiment, conductor assembly $540e_0$ includes a conductive loop which is arranged to form five diamond-shaped structures $540e2$ interconnected by conductors $540e_1$. Preferably, the conductive structure $540e_2$ is located centrally between four adjacent fingers 532 in a two-by-two portion of the overall evaporator assembly.

Returning now to FIG. 4, the cooler-heater remote unit (300) provides the operator interface and control signals via a hardwired tether 302 of any appropriate length (e.g., 5 meters), which allows the user to place the remote unit 300 in a location of their choosing for ready access. The remote unit 300 may be used on either the refrigeration or ice units interchangeably, or in combination. A color touch panel display 306 on a face of the unit housing 304 provides the entire operator interface for either of the different local units. The remote unit may be pole mounted and tethered to the local unit 100 by an electrical cable, such as tether 302, to allow communication with the local unit 100, or may communicate with the local unit 100 remotely in a wireless manner. In the event that the remote and local units are in hard-wire communication with each other, such communication cabling is typically hard-wired at the remote unit 300 and utilizes a connector on one face of the local unit 100. DC power from the Local Unit 100 is supplied by the cable to the remote and input/control signals flow to and from each unit.

The modular support device includes caster mounts 132 for casters 134 in a variety of distinct configurations. In FIG. 2, a single wheel set configuration to mount one local unit is shown, while in FIG. 3, a dual wheel set to mount two local units, such as a refrigeration unit or an ice unit, are shown. The operator can configure their cooler-heater devices in whatever is appropriate so as to meet specific clinical needs (e.g., more cooling for cardioplegia) or, alternatively, the operator can utilize the different wheel sets to separate or join the local units to meet operating room space constraints.

The modular design of the cooler-heater system 100 allows an operator to configure the system to best meet the patients' needs and the physical constraints of the modern crowded operating room environment.

Pump rates can range from about 5 mL/kg to about 20 mL/kg, inclusive, as appropriate, depending upon the size and type of patient, or alternatively at a rate up to a maximum of about 60 lpm (Liters per minute), as appropriate. Exemplary pump rates include but are not limited to about 5 mL/kg (of weight of the patient), about 7 mL/kg, about 9 mL/kg, about 12 mL/kg, about 15 mL/kg, and about 18 mL/kg, as well as pump rates between any of these rates, or over a flexible range (e.g., from about 6 mL/kg to about 10 mL/kg) of time.

Figure 4:
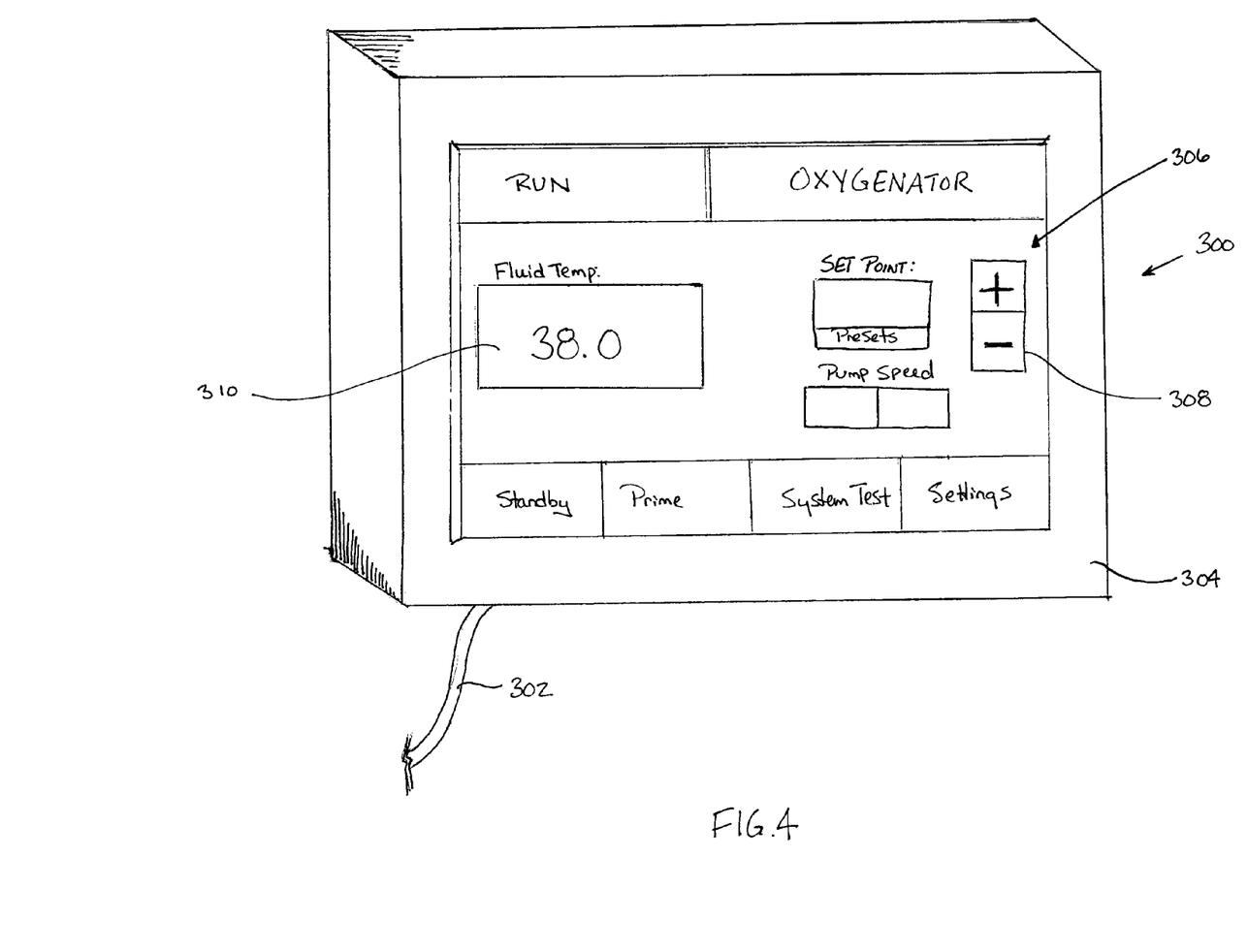
FIG. 4 illustrates an exemplary remote control unit in association with the systems of the present disclosure.

The Modular Cooler-Heater (MCH) employs "Adaptive Temperature Control" (ATC) that is unique to this device. The adaptive temperature control of the present system is used to achieve greater temperature accuracy by achieving and maintaining the operator-selected fluid temperature, which in turn assists in controlling the patient's body temperature more precisely, therefore providing better patient outcomes post open-heart surgery. This control is provided by a software system as described herein, where the software can be stored on a computer-readable storage medium inside a computer system, such as the control unit 300.

The ATC function is based on a short-term time differential of the fluid (e.g., water or salt-water) temperature in a circulating loop. Using this temperature differential, the function adjusts heater cutoff timing (in adaptive re-warm mode) and cooling valve activation timing (in adaptive cooling mode) so that the output water temperature reaches the set temperature as quickly and efficiently as possible, without overshooting or undershooting the set temperature.

An "adaptive re-warm" protocol takes into consideration the load placed on the heater circuit by the patient size, heat exchanger performance, room temperature and rate of fluid flow by calculating the rate of fluid temperature change in the system, therefore adjusting the heater cutoff temperature. This adjustment keeps the temperature from overshooting. Temperature overshoot begins a "porpoise" sequence in which the temperature overshoots then undershoots in a repeating cycle until the temperature stabilizes. The adaptive temperature control in accordance with this invention controls this adverse cycle from starting by controlling overshoot, therefore enhancing patient outcome.

Adaptive re-warm sets the heater cutoff timing by first calculating a temperature change factor y by taking a running three-second differential of the fluid (water) temperature T $(T_t - T_{t-3})$ and multiplying by an adjustment x:

$$y=(T_t-T_{t-3})\cdot x$$

The temperature change factor is then used to determine the temperatures at which the primary and secondary heaters are turned off:

$$\Delta_{h1}=y$$

$$\Delta_{h2}=3y-1/y$$

$$T1_{cutoff}=T_{set}-\Delta_{h1}$$

$$T2_{cutoff}=T_{set}-\Delta_{h2}$$

When the water temperature reaches T1, heater 1 is turned off (at $T1_{cutoff}$). When the water temperature reaches T2, heater 2 is turned off (at $T2_{cutoff}$).

Adaptive cooling works in reverse of Adaptive re-warm as it controls the cooling valve turn-on time. By adjusting the turn-on time of the cooling valve the ATC system keeps from initiating large water temperature drops. These large temperature drops start the temperature "porpoise sequence" mentioned above, that are adverse to patient outcome.

To set the cooling valve activation timing, the system calculates the difference between the current water temperature and the set (or desired) temperature ($T_{set}$), and multiplying by an adjustment, z:

$$t_{open}=|T-T_{set}|\cdot z$$

The cooling valve is then opened for $t_{open}$ seconds. The cooling valve is then disabled for a short period of time to allow the water temperature to stabilize before recalculating $t_{open}$.

The cooling-heating software used in the instant application also detects when the unit does not have enough cooling capacity to lower the water to the set temperature, and triggers a "low ice" alarm in this situation. This is accomplished by tracking the water temperature and noting whether or not it dips below the set temperature at any point. If this does not occur within 35 seconds, the alarm is triggered. These features are advantageous in that the system can be set and does not require an individual to constantly monitor the temperature, and the patient's temperature remains substantially stable during the surgical operation.

The remote unit 300 of the system 100 of the present disclosure includes not only the software described above, but also comprises an interactive display assembly 306 for use by the operator. In accordance with aspects of the present disclosure, display 306 may be a color liquid crystal display suitable to provide the user with up-to-the-second information and quick temperature response. A plurality of interactive buttons, such as the +/− buttons 308 allow for fine temperature adjustments during system operation. A current temperature indicator 310 allows the user to see the current fluid temperature during system use. In typical use, a user selects a temperature set-point, and a numeric keypad appears on the display 306 to allow the user to enter the desired temperature. Alternatively, and equally acceptable, the system may include a plurality of custom preset temperatures (e.g., 0° C., 5° C., 15° C., and 32° C.) to store common temperature settings for ultra-fast access. A tether 302 allows the user to put the touchscreen display 306 where it is most useful, whether that be attached directly to handle 112 of the system 100, or attached to another device within the operating room, such as a heart-lung machine. In accordance with further aspects of the current disclosure, the remote unit may also have wireless capabilities, allowing the software and interactive display screen of the unit to directly interact with the local cooling unit 100.

The modular cooler-heater system 100 may also include other features, such as a "low ice" alarm, as well as a convenient recirculation valve to facilitate a "hot shot" during cardioplegia, as appropriate.

Applications:

The systems described herein may be used in association with a variety of surgical procedures, including but not limited to cardiopulmonary by-pass operations, epidural perfusions, replacement of all or part of a thoracic aorta or thoracoabdominal aorita, a cardiovascular procedure, a laparoscopic surgical procedure requiring surgical cooling, a nephrectomy, or any other surgical procedure where arterial perfusion to cool an organ or region of the patient undergoing the surgery is advantageous.

Other and further embodiments utilizing one or more aspects of the inventions described above can be devised without departing from the spirit of Applicant's invention. For example, different arrangements and organizations of the system may be included. Further, the various methods and embodiments of the disclosure can be included in combination with each other to produce variations of the disclosed methods and embodiments. Discussion of singular elements can include plural elements and vice-versa.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to fully protect all such modifications and improvements that come within the scope or range of equivalent of the following claims.

What is claimed is:

1. A modular support and mobility device for a modular patient cooling-heating system, comprising:
   at least one modular patient cooling-heating system fluid reservoir having a front wall, the front wall comprising a component configured to function as a handle for directing the movement of the modular support and mobility device and also configured to removably mount a patient cooling-heating system control unit;
   a chassis having a mounting surface disposed between a first and second opposed chassis ends, and configured to removably support a bottom of the at least one or more modular patient cooling-heating system fluid reservoirs with the front wall interchangeably associated with the first end or the second end;
   a plurality of casters attached to the chassis and configured to provide mobility when the one or more modular patient cooling-heating system fluid reservoirs are mounted on the chassis;
   a plurality of retaining mechanisms associated with the chassis and configured to removably retain the one or more modular patient cooling-heating system fluid reservoirs; and
   the modular support and mobility device configured to removably support at least one of a blood reservoir, a blood oxygenator, and a blood filter.

2. The support and mobility device of claim 1, further comprising a plurality of openings in the chassis.

3. The support and mobility device of claim 2 wherein the retaining mechanisms are selected from the group consisting of straps, hooks, hook and loop fasteners, and combinations of same.

4. The support and mobility device of claim 2 in which the openings are configured to support one or more of the blood reservoir, blood oxygenator, and blood filter.

5. The support and mobility device of claim 4, wherein the chassis comprises a generally planar body and is reversible so that the at least one of the blood reservoir, blood oxygenator, and blood filter may be supported in and displayed by the openings from either side of the planar body.

6. The support and mobility device of claim 1, wherein the chassis is rigid.

7. The support and mobility device of claim 1, wherein the chassis is planar.

8. The support and mobility device of claim 1, wherein the chassis is flexible.

9. The support and mobility device of claim 1, wherein the chassis is formed of a polymer.

10. The support and mobility device of claim 9, wherein the polymer is non-brittle and non-abrasive, and is sterilizable.

11. The support and mobility device of claim 1 wherein the chassis is configured to support one modular patient cooling-heating system fluid reservoir, a blood reservoir, a blood oxygenator, and a blood filter.

12. The support and mobility device of claim 1 wherein the chassis is configured to interchangeably support two modular patient cooling-heating system fluid reservoirs, a blood reservoir, a blood oxygenator, and a blood filter.

* * * * *